(12) United States Patent
Takai et al.

(10) Patent No.: US 10,001,498 B2
(45) Date of Patent: Jun. 19, 2018

(54) SAMPLE SORTING APPARATUS, SAMPLE PROCESSING SYSTEM, AND SAMPLE SORTING METHOD

(71) Applicant: Sysmex Corporation, Kobe-shi, Hyogo (JP)

(72) Inventors: Kei Takai, Kobe (JP); Nobuyoshi Yamakawa, Kobe (JP); Koichi Okubo, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 886 days.

(21) Appl. No.: 14/028,194

(22) Filed: Sep. 16, 2013

(65) Prior Publication Data

US 2014/0079527 A1 Mar. 20, 2014

(30) Foreign Application Priority Data

Sep. 20, 2012 (JP) .................. 2012-207498

(51) Int. Cl.
*G01N 35/02* (2006.01)
*G01N 35/04* (2006.01)

(52) U.S. Cl.
CPC .......... *G01N 35/026* (2013.01); *G01N 35/04* (2013.01); *G01N 2035/0462* (2013.01); *G01N 2035/0465* (2013.01)

(58) Field of Classification Search
CPC ...... G01N 35/02; G01N 35/04; G01N 35/026; G01N 2035/0462; G01N 2035/0465
See application file for complete search history.

(56) References Cited

U.S. PATENT DOCUMENTS

| 6,068,437 A | 5/2000 | Boje et al. |
| 6,255,614 B1 | 7/2001 | Yamakawa et al. |
| 6,926,058 B2* | 8/2005 | Sato ............. G01N 35/04 |
| | | 156/539 |

(Continued)

FOREIGN PATENT DOCUMENTS

| EP | 2 175 279 A1 | 4/2010 |
| EP | 2 693 220 A2 | 2/2014 |

(Continued)

*Primary Examiner* — Anna M Momper
*Assistant Examiner* — Ashley K Romano
(74) *Attorney, Agent, or Firm* — Brinks Gilson & Lione

(57) ABSTRACT

A sample sorting apparatus used in a sample processing system comprises a sample supplying apparatus, a sample processing apparatus, and a transporting apparatus connected to the sample processing apparatus. The sample sorting apparatus comprises a first entrance for receiving a sample rack from the sample supplying apparatus, a container conveyor configured to take out a sample container from the sample rack received through the first entrance and configured to set the taken out sample container on a sample rack, a first exit for sending the sample rack on which the sample container is set to the transporting apparatus, a second entrance for receiving the sample rack from the transporting apparatus, a second exit for sending the sample rack received through the second entrance to the sample supplying apparatus, and a transporter configured to transport the sample rack from the second entrance to the second exit.

12 Claims, 14 Drawing Sheets

(56) References Cited

U.S. PATENT DOCUMENTS

| | | | |
|---|---|---|---|
| 7,360,984 B1* | 4/2008 | Sugiyama | B01L 9/543 414/798.1 |
| 7,448,487 B2* | 11/2008 | Koike | G01N 35/026 198/349 |
| 9,110,043 B2* | 8/2015 | Kaneko | G01N 35/025 |
| 9,176,155 B2* | 11/2015 | Yamato | G01N 35/026 |
| 9,213,041 B2* | 12/2015 | Kitagawa | G01N 35/026 |
| 9,222,952 B2* | 12/2015 | Tatsutani | G01N 35/0092 |
| 9,229,017 B2* | 1/2016 | Kitagawa | G01N 35/0092 |
| 2006/0216198 A1* | 9/2006 | Koike | G01N 35/026 422/65 |
| 2012/0009087 A1 | 1/2012 | Okubo | |
| 2014/0037517 A1* | 2/2014 | Takai | B01L 9/06 422/562 |
| 2014/0212248 A1* | 7/2014 | Takai | G01N 35/04 414/273 |

FOREIGN PATENT DOCUMENTS

| | | |
|---|---|---|
| JP | 2002-040034 A | 2/2002 |
| JP | 2002-090374 A | 3/2002 |
| JP | 2009-222535 A | 10/2009 |
| JP | 2010-032518 A | 2/2010 |
| JP | 2010-175513 A | 8/2010 |
| JP | 2012-018144 A | 1/2012 |
| WO | WO 2007/139212 A1 | 12/2007 |

\* cited by examiner

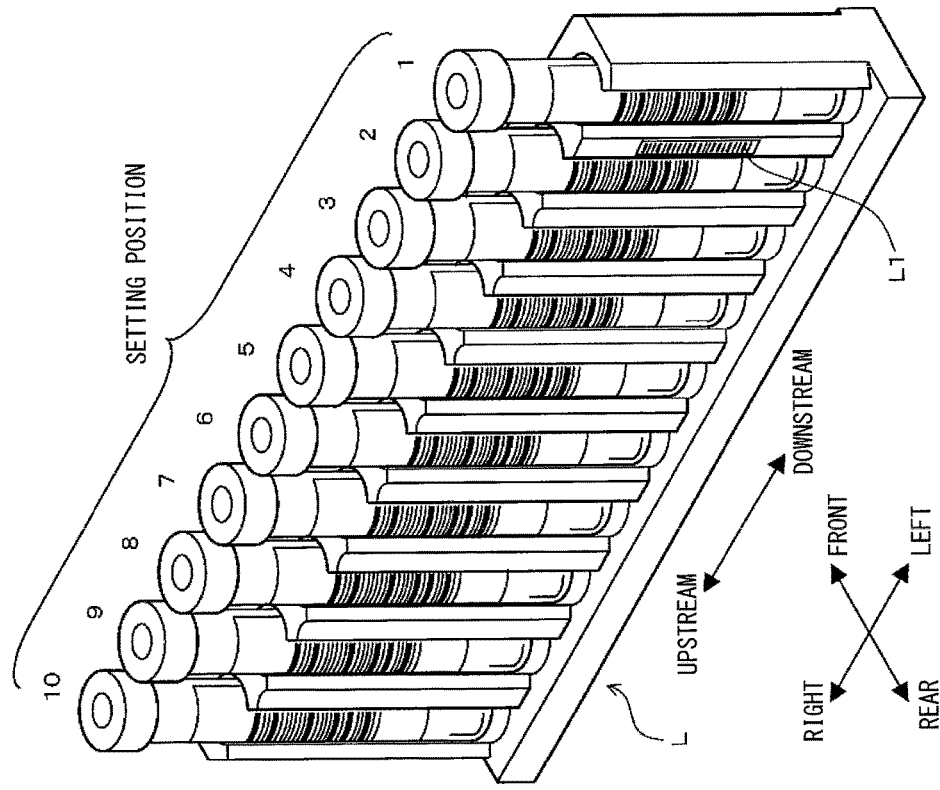
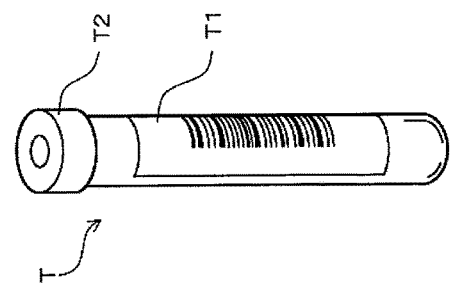

F I G. 7
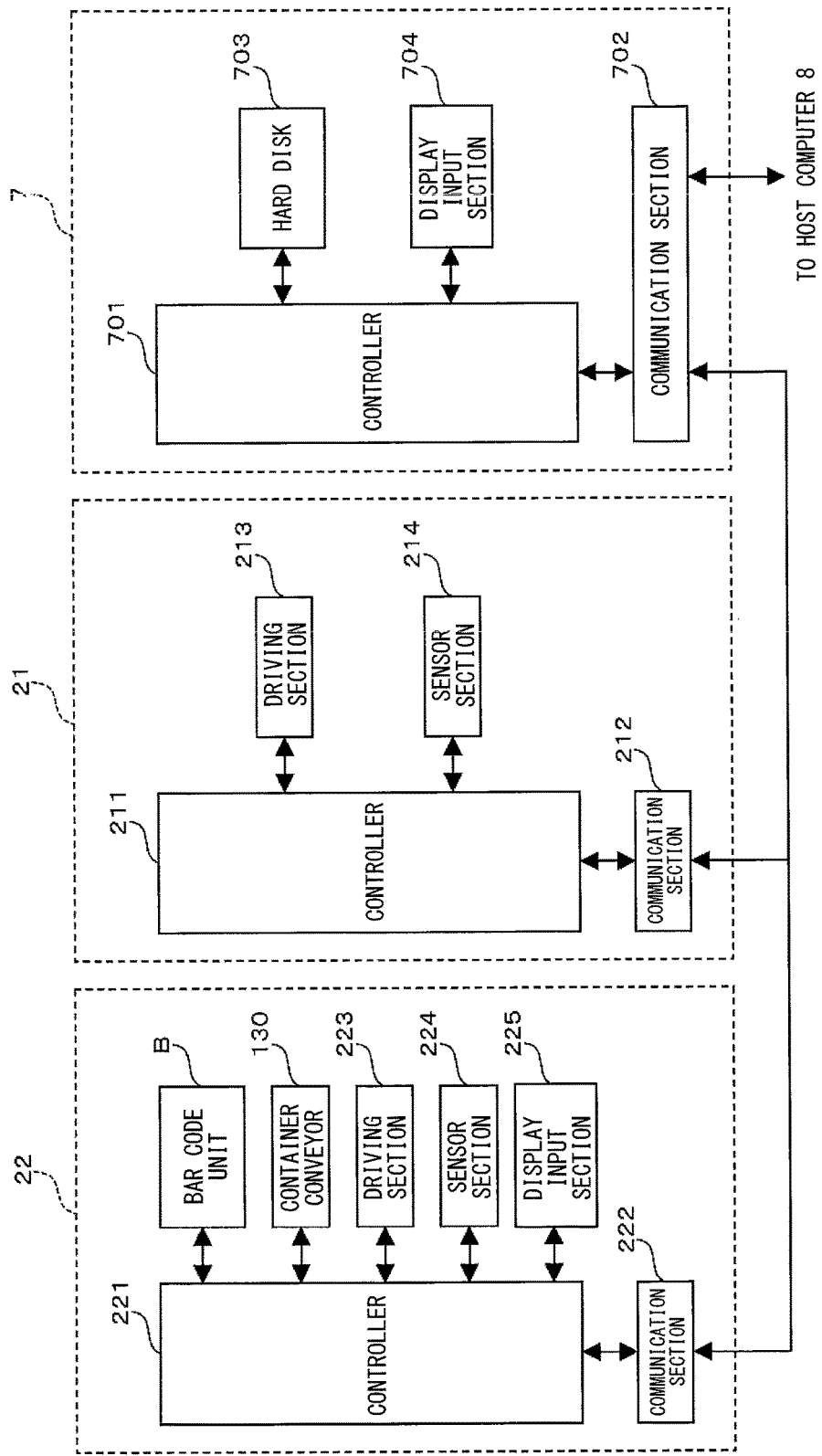

SAMPLE SORTING APPARATUS, SAMPLE PROCESSING SYSTEM, AND SAMPLE SORTING METHOD

RELATED APPLICATIONS

This application claims priority under 35 U.S.C. § 119 to Japanese Patent Application No. 2012-207498 filed on Sep. 20, 2012, the entire content of which is hereby incorporated by reference.

BACKGROUND OF THE INVENTION

1. Field of the Invention

The present invention relates to a sample sorting apparatus that can transfer a sample container from one sample rack to another sample rack, and a sample processing system including the sample sorting apparatus.

2. Description of the Related Art

To date, there are known sample processing systems that process samples such as blood and urine. For example, in a sample processing system described in U.S. Patent Application Publication No. 2012/0009087 A, by a transporting apparatus transporting a sample rack holding sample containers, samples contained in the sample containers are transported to a sample processing apparatus.

SUMMARY OF THE INVENTION

Further, in a sample processing system described in Japanese Laid-Open Patent Application No. 2002-040034, there is disclosed a sorting apparatus that automatically sorts sample containers into predetermined sample racks in accordance with the types of processes therefor prior to sample processing in order to efficiently process a large number of samples. Further, in a sorting apparatus described in Japanese Laid-Open Patent Application No. 2009-222535, after sample processing is performed, sample containers are automatically sorted into predetermined sample racks, in accordance with the results of the processing and the contents of the next processing.

When such a sorting apparatus is applied to a sample processing system described in U.S. Patent Application Publication No. 2012/0009087 A, it is necessary to individually secure a region in which each sorting apparatus is installed. Therefore, there arises a problem that an installation area for the entire sample processing system is increased.

The scope of the present invention is defined solely by the appended claims, and is not affected to any degree by the statements within this summary.

A first aspect of the present invention is a sample sorting apparatus used in a sample processing system comprises a sample supplying apparatus, a sample processing apparatus, and a transporting apparatus connected to the sample processing apparatus. The sample sorting apparatus comprises a first entrance for receiving a sample rack from the sample supplying apparatus, a container conveyor configured to take out a sample container from the sample rack received through the first entrance and configured to set the taken out sample container on a sample rack, a first exit for sending the sample rack on which the sample container is set to the transporting apparatus, a second entrance for receiving the sample rack from the transporting apparatus, a second exit for sending the sample rack received through the second entrance to the sample supplying apparatus, and a transporter configured to transport the sample rack from the second entrance to the second exit.

A second aspect of the present invention is a sample processing system comprising: a sample sorting apparatus; a sample supplying apparatus which supplies a sample rack to the sample sorting apparatus; a sample processing apparatus which processes a sample in a sample container held in a sample rack; and a transporting apparatus arranged between the sample sorting apparatus and the sample processing apparatus. The sample sorting apparatus comprises: a first entrance for receiving a sample rack from the sample supplying apparatus; a container conveyor configured to take out a sample container from the sample rack received through the first entrance and configured to set the taken out sample container, on a sample rack; a first exit for sending the sample rack on which the sample container is set, to the transporting apparatus; a second entrance for receiving the sample rack from the transporting apparatus; a second exit for sending the sample rack received through the second entrance to the sample supplying apparatus; and a transporter configured to transport the sample rack from the second entrance to the second exit. The sample supplying apparatus sends out a sample rack through the first entrance to the sample sorting apparatus, and receives a sample rack sent out through the second exit. The transporting apparatus transports a sample rack sent out through the first exit, to the sample processing apparatus, and transports a sample rack for which processing in the sample processing apparatus has been completed, to the second entrance.

A third aspect of the present invention is a sample sorting method used in a sample processing system comprising a sample supplying apparatus, a sample processing apparatus, a transporting apparatus connected to the sample processing apparatus, and a sample sorting apparatus. The sample sorting method comprises: receiving a sample rack through a first entrance from the sample supplying apparatus, by the sample sorting apparatus; taking out a sample container from the sample rack received through the first entrance, by the sample sorting apparatus; setting the taken out sample container on a sample rack, by the sample sorting apparatus; sending the sample rack on which the sample container is set, to the transporting apparatus through a first exit, by the sample sorting apparatus; receiving again, through a second entrance, the sample rack sent to the transporting apparatus through the first exit, by the sample sorting apparatus; and sending the sample rack received through the second entrance, to the sample supplying apparatus through a second exit, by the sample sorting apparatus.

BRIEF DESCRIPTION OF THE DRAWINGS

FIGS. 2A and 2B show structures of a sample container and a sample rack according to an embodiment;

FIG. 7 shows an outline of the configuration of the feeding unit, the sample sorting apparatus, and a transport controller according to an embodiment;

DETAILED DESCRIPTION OF THE PREFERRED EMBODIMENTS

The preferred embodiments of the present invention will be described hereinafter with reference to the drawings.

Figure 1:
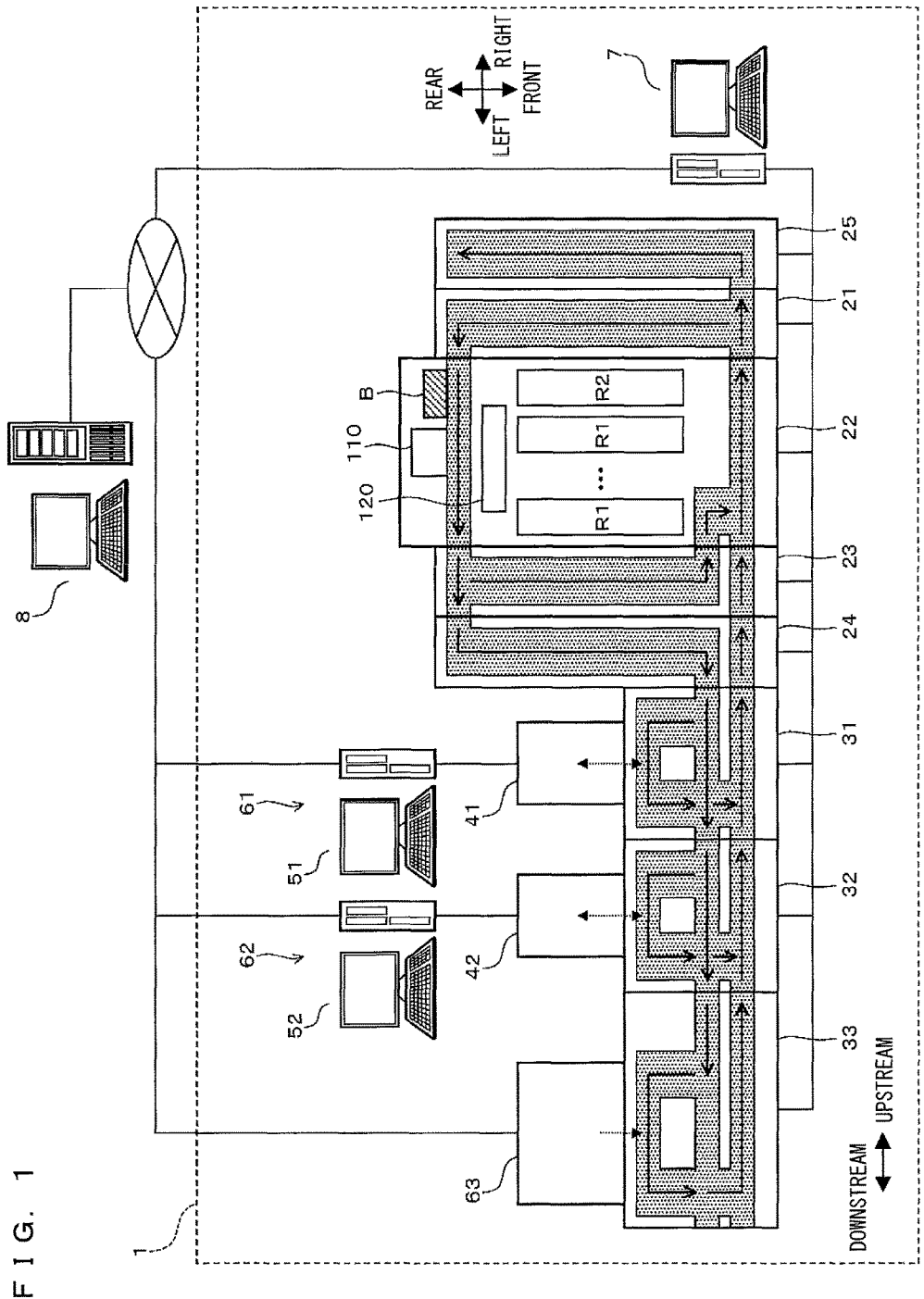
FIG. 1 shows a structure of a sample processing system according to an embodiment viewed from above.

FIG. 1 shows a structure of a sample processing system 1 viewed from above.

The sample processing system 1 according to the present embodiment includes a feeding unit 21, a sample sorting apparatus 22, a relay unit 23, a preprocessing unit 24, a collection unit 25, transporting units 31 to 33, blood cell analyzers 61 and 62, a smear preparing apparatus 63, and a transport controller 7. The blood cell analyzer 61 includes an information processing unit 51 and a measurement unit 41. The blood cell analyzer 62 includes an information processing unit 52 and a measurement unit 42. The sample processing system 1 is communicably connected to a host computer 8 via a communication network.

The feeding unit 21, the sample sorting apparatus 22, the relay unit 23, the preprocessing unit 24, the collection unit 25, and the transporting units 31 to 33 are arranged adjacent to each other in the left-right direction such that a sample rack L can be transported therebetween. Further, each of the units and apparatus is configured such that a plurality of sample racks L, each capable of holding ten sample containers T, can be placed thereon, and such that each sample rack L can be transported along the arrows shown in FIG. 1.

FIGS. 2A and 2B show structures of a sample container T and a sample rack L, respectively. FIG. 2A is a perspective view showing an external view of a sample container T, and FIG. 2B is a perspective view showing an external view of a sample rack L holding ten sample containers T. FIG. 2B also shows the orientation (front, rear, left, and right directions shown in FIG. 1) of the sample rack L when it is transported.

With reference to FIG. 2A, the sample container T is a tubular container made of glass or synthetic resin having translucency, and its upper end is open. A bar code label T1 is attached to a lateral surface of the sample container T. A bar code including a sample ID is printed on the bar code label T1. The sample container T contains a whole blood sample collected from a patient, and the opening at the upper end thereof is sealed with a rubber cap T2. With reference to FIG. 2B, a bar code label L1 is attached to a lateral surface on the rear side of the sample rack L. A bar code including a rack ID is printed on the bar code label L1. Further, holders capable of vertically holding ten sample containers T are formed in the sample rack L.

With reference back to FIG. 1, when starting measurement of sample(s), a user sets one or more sample containers T each containing a sample on a sample rack L, and places this sample rack L in the feeding unit 21. When supplying an empty sample rack L to an empty rack stocker 110 of the sample sorting apparatus 22, the user places the empty sample rack L in the feeding unit 21. The sample rack L placed in the feeding unit 21 is transported rearward, and sent out to the sample sorting apparatus 22.

The sample sorting apparatus 22 first performs a process by a bar code unit B, with respect to the sample rack L that has been sent out from the feeding unit 21 to the sample sorting apparatus 22. Specifically, the bar code unit B reads a rack ID from the bar code label L1 of the sample rack L, and reads a sample ID from the bar code label T1 of each sample container T. The sample sorting apparatus 22 transmits each sample ID read by the bar code unit B to the host computer 8 via the transport controller 7. Based on a measurement order set for each sample, an analysis result of the sample, and the like, the host computer 8 generates information (hereinafter referred to as "transfer information") for transferring its corresponding sample container T within the sample sorting apparatus 22. Then, the sample sorting apparatus 22 receives the transfer information from the host computer 8 via the transport controller 7.

Subsequently, the sample sorting apparatus 22 transfers sample container(s) T held in the sample rack L, into a buffer rack 120, archive racks R1, and a sorting rack R2, in accordance with the received transfer information. Further, the sample sorting apparatus 22 transfers sample container(s) T held in the buffer rack 120 into a sample rack L as appropriate. Then, this sample rack L is sent out to the relay unit 23. In a case where the sample container(s) T are all taken out and the sample rack L has become empty, and in a case where the sample rack L has been empty from the beginning, this sample rack L will be stocked in the empty rack stocker 110 if the empty rack stocker 110 has a vacancy, or is sent out to the relay unit 23 if the empty rack stocker 110 is full.

When the sample rack L sent out from the sample sorting apparatus 22 to the relay unit 23 is to be transported leftward, it is sent out to the preprocessing unit 24, and when the sample rack L is to be transported rightward, it is transported forward in the relay unit 23 to be sent out to the sample sorting apparatus 22. The sample rack L sent out from the relay unit 23 to the preprocessing unit 24 is transported forward in the preprocessing unit 24, and then, sent out to the transporting unit 31.

Each of the transporting units 31 to 33 transports a sample rack L sent out from the upstream side, in accordance with an instruction from the transport controller 7. Specifically, each of the transporting units 31 to 33 transports, in a case where processing is performed in its corresponding unit or apparatus, a sample rack L sent out from the upstream side, rearward, to a front position facing its corresponding unit or apparatus. In a case where processing is performed neither in the measurement unit 41 nor 42, each of the transporting units 31 and 32 causes a sample rack L sent out from the upstream side, to advance directly leftward, and sequentially sends it out to its downstream transporting unit.

Each of the measurement units 41 and 42 takes out a sample container T from the sample rack L transported to its front position, and measures the sample contained in this sample container T. Each of the information processing units 51 and 52 receives measurement data of a sample from the corresponding one of the measurement units 41 and 42 to analyze the measurement data, and generates an analysis result containing analysis values of respective measurement items. Further, the information processing units 51 and 52 are communicably connected to the host computer 8 and transmit analysis results to the host computer 8.

The smear preparing apparatus 63 aspirates, at its front position, a sample from a sample container T held in a sample rack L, and prepares a smear of the aspirated sample. Further, the smear preparing apparatus 63 is communicably connected to the host computer 8, and transmits to the host computer 8 information indicating that smear preparation has been completed.

When the processing by each of the measurement units 41 and 42 and the smear preparing apparatus 63 has been completed, and there is no need to perform processing on the downstream side any more, each sample rack L is transported forward in the transporting unit by which the sample rack L is being transported, and then sent out to the upstream side by this transporting unit. In this manner, each sample rack L is sequentially transported in the upstream direction.

The sample rack L which has been sequentially transported from the transporting units 31 to 33 to the upstream side is further transported rightward by the preprocessing unit 24 and the relay unit 23, and then sent out to the sample sorting apparatus 22. The sample sorting apparatus 22 sends out the sample rack L sent in from the relay unit 23, to the feeding unit 21.

The sample rack L sent out from the sample sorting apparatus 22 to the feeding unit 21 is transported rearward in the feeding unit 21, and is sent out to the sample sorting apparatus 22 again. Also in this case, similarly to the above, reading by the bar code unit B is performed, and the sample sorting apparatus 22 receives transfer information from the host computer 8, and transfers sample container(s) T held in the sample rack L, in accordance with the received transfer information.

Thus, a sample container T that needs neither retests by the measurement units 41 and 42 nor smear preparation performed by the smear preparing apparatus 63 again (hereinafter simply referred to as "retesting") and that does not need processing performed in an apparatus other than the sample processing system 1 is transferred to one of the archive racks R1, in accordance with its transfer information. A sample container T that does not need retesting but needs processing in an apparatus other than the sample processing system 1 is transferred to the sorting rack R2. A sample container T that needs retesting is transferred to a sample rack L as appropriate, similarly to the above, and then, is sent out to the relay unit 23. The processing of a sample container T by the sample processing system 1 is completed, by the sample container T being transferred to one of the archive racks R1 or the sorting rack R2.

An empty sample rack L sent out from the sample sorting apparatus 22 to the relay unit 23 is transported forward in the relay unit 23, and then sent out to the sample sorting apparatus 22. The sample sorting apparatus 22 sends out the empty sample rack L that has been sent in from the relay unit 23, to the feeding unit 21. The empty sample rack L sent out from the sample sorting apparatus 22 to the feeding unit 21 is transported rightward by the feeding unit 21, to be sent out to the collection unit 25. Then, this sample rack L is transported rearward in the collection unit 25 to be housed in the collection unit 25. Thus, transportation of the sample rack L is completed.

The transport controller 7 is communicably connected to the feeding unit 21, the sample sorting apparatus 22, the relay unit 23, the preprocessing unit 24, the collection unit 25, and the transporting units 31 to 33, and controls transporting operations of a sample rack L performed by these. The host computer 8 has stored therein, associated with each sample ID, a measurement order of the sample corresponding to the sample ID, analysis results of this sample, and the like. Moreover, the host computer 8 retains a rule for transferring a sample container T within the sample sorting apparatus 22.

Figure 3:
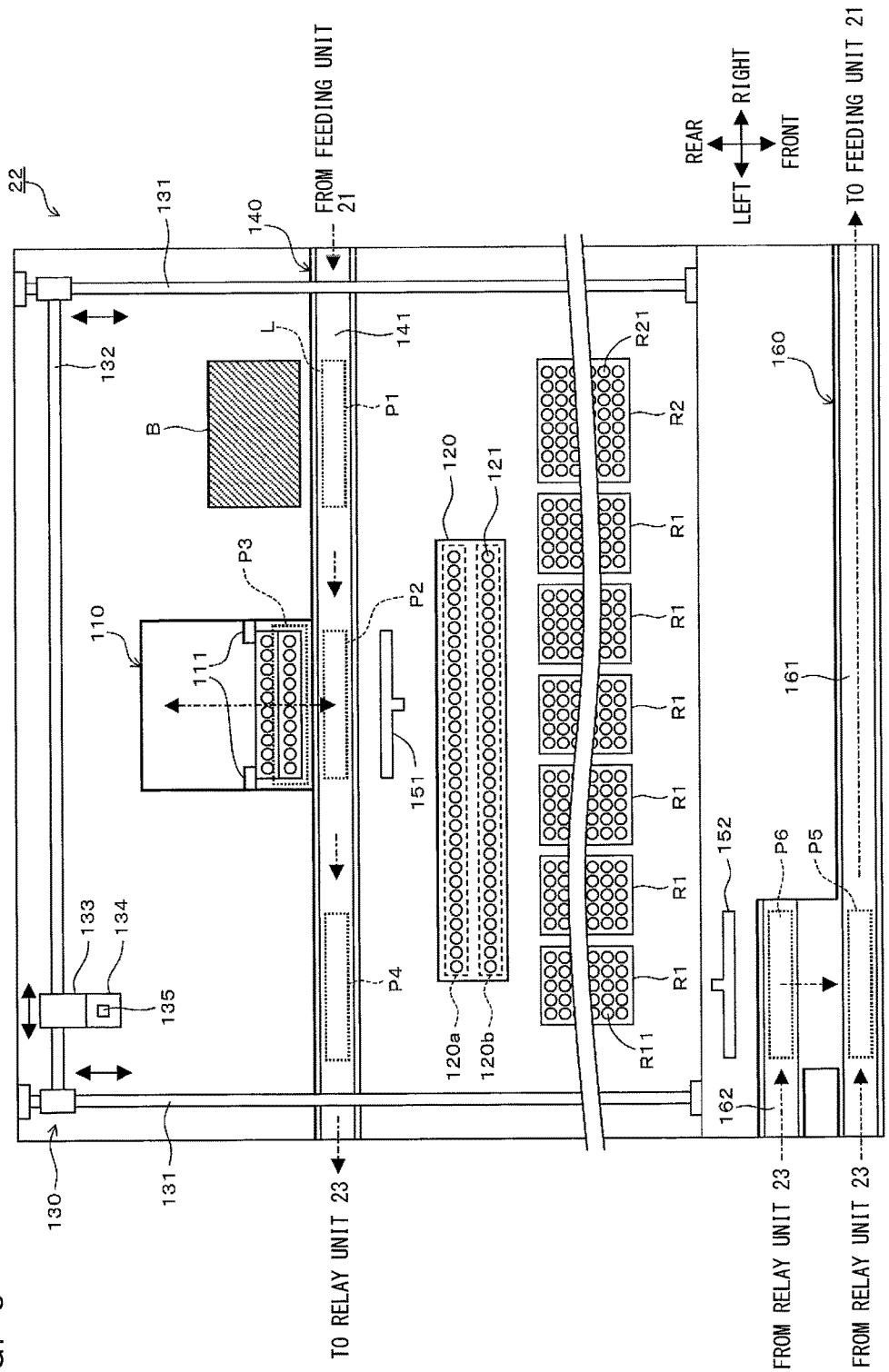
FIG. 3 shows a structure of the inside of a sample sorting apparatus according to an embodiment viewed from above.

FIG. 3 shows a structure of the inside of the sample sorting apparatus 22 viewed from above.

The sample sorting apparatus 22 is provided with a container conveyor 130 for conveying a sample container T within the sample sorting apparatus 22. The container conveyor 130 includes: two guides 131 fixed inside the sample sorting apparatus 22 and extending in the front-rear direction; a guide 132 extending in the left-right direction and slidable in the front-rear direction along the guides 131; a sliding part 133 slidable in the left-right direction along the guide 132; an ascending/descending part 134 set in the sliding part 133 and capable of ascending/descending relative to the sliding part 133; a gripper 135 set at the lower end of the ascending/descending part 134 and capable of gripping a sample container T; and a mechanism for driving these parts. It should be noted that the guides 131 are located at a higher level than a transporter 140.

The buffer rack 120 is provided with 60 holders 121. In the buffer rack 120, a region 120a including 30 holders 121 on the rear side and a region 120b including 30 holders 121 on the front side are set. Each archive rack R1 is provided with 125 holders R11, and the sorting rack R2 is provided with 250 holders R21.

A sample rack L sent out from the feeding unit 21 is transported leftward by a belt 141 of the transporter 140 to be located at a position P1 facing the bar code unit B. The bar code unit B reads the rack ID and each sample ID. As described above, the sample sorting apparatus 22 transmits each sample ID that has been read, to the host computer 8 and receives transfer information from the host computer 8. Upon completion of reading by the bar code unit B, the sample rack L is transported leftward to be located at a position P2. With the sample rack L being located at the position P2, sample container(s) T held in this sample rack L are transferred by the container conveyor 130, in accordance with their transfer information.

The transfer information includes a transfer destination within the sample sorting apparatus 22 of a sample container T. Specifically, when the transportation destination of a sample container T is the measurement unit 41, the transfer information is "no transfer". When the transportation destination of a sample container T is the measurement unit 42, the transfer information is "buffer rack region 120a". When the transportation destination of a sample container T is the smear preparing apparatus 63, the transfer information is "buffer rack region 120b". When the transportation destination of a sample container T is an apparatus that is none of the measurement units 41 and 42 and the smear preparing apparatus 63 (hereinafter referred to as "another apparatus"), or when another process such as observation under a microscope, etc. is scheduled, the transfer information is "sorting rack". When the transportation destination of a sample container T is none of the measurement units 41 and 42, the smear preparing apparatus 63, and another apparatus, and no other process is scheduled, the transfer information is "archive rack". When the transfer information of a sample container T is "buffer rack region 120*a*", "buffer rack region 120*b*", "archive rack", or "sorting rack", this sample container T is accordingly transferred to a holder 121 in the region 120*a* of the buffer rack 120, a holder 121 of the region 120*b* of the buffer rack 120, a holder R11 of one of the archive racks R1, or a holder R21 of the sorting rack R2.

In a case where a sample rack L from which all the sample container(s) T have been taken out at the position P2 and has become empty, or a sample rack L that has been empty from the beginning and has been transported from the position P1 to the position P2 is to be conveyed to the empty rack stocker 110, the sample rack L is pushed out to a position P3, which is in a front portion of the empty rack stocker 110, by the front side face of this sample rack L being pushed by a rack pushing-out mechanism 151. On the other hand, an empty sample rack L located at the position P3 is sent to the position P2, by the rear side face of the rearmost sample rack L in the empty rack stocker 110 being pushed by a rack sending-in mechanism 111.

Into an empty sample rack L located at the position P2, sample container(s) T held in the region 120*a* or 120*b* of the buffer rack 120 are transferred by the container conveyor 130 as appropriate. When the sample rack L located at the position P2 is to be conveyed to the downstream side, the sample rack L is transported leftward by the belt 141 to be located at a position P4. The sample rack L located at the position P4 is transported leftward by the belt 141, to be sent out to the relay unit 23.

Here, a sample rack L that holds only sample container(s) T that were not transferred at the position P2 is transported to the measurement unit 41, and is subjected to measurement by the measurement unit 41. Meanwhile, a sample rack L into which sample container(s) T held in the region 120*a* of the buffer rack 120 have been transferred is transported to the measurement unit 42, and is subjected to measurement by the measurement unit 42. Further, a sample rack L into which sample container(s) T held in the region 120*b* of the buffer rack 120 have been transferred is transported to the smear preparing apparatus 63, and is subjected to smear preparation by the smear preparing apparatus 63. That is, the regions 120*a* and 120*b* are regions for temporarily holding sample containers T to be transported to the measurement unit 42 and the smear preparing apparatus 63, respectively, and sample container(s) T that remain in a sample rack L without being transferred to these regions are transported to the measurement unit 41, and are subjected to measurement by the measurement unit 41.

Next, a sample rack L sent in from the relay unit 23 to a transporter 160 is transported rightward by a belt 161 or a belt 162 of the transporter 160, and is located at a position P5 or a position P6. The sample rack L located at the position P6 is then located at the position P5 by the rear side face of the sample L being pushed by a rack pushing-out mechanism 152. The sample rack L located at the position P5 is transported rightward by the belt 161, to be sent out to the feeding unit 21.

Figure 4:
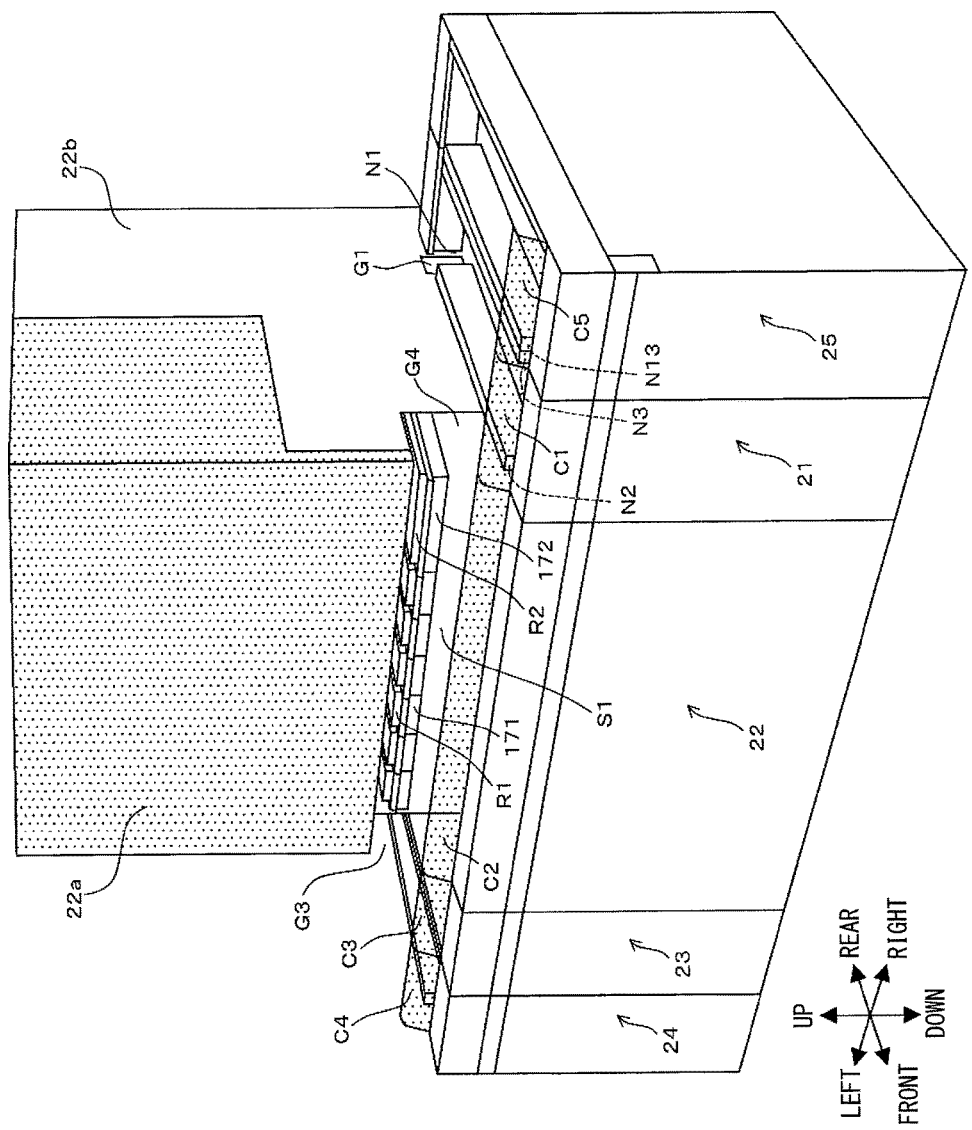
FIG. 4 is a perspective view showing external structures of a feeding unit, the sample sorting apparatus, a relay unit, a preprocessing unit, and a collection unit according to an embodiment.

FIG. 4 is a perspective view showing external structures of the feeding unit 21, the sample sorting apparatus 22, the relay unit 23, the preprocessing unit 24, and the collection unit 25.

In front portions of the feeding unit 21, the sample sorting apparatus 22, the relay unit 23, the preprocessing unit 24, and the collection unit 25, covers C1 to C5 are provided so as to prevent a user from touching a sample rack L that is being transported. Each of the covers C1 to C5 is configured to be able to be turned forward. Further, the sample sorting apparatus 22 is provided with a front cover 22*a*, at the front face thereof. The user can access the inside of the sample sorting apparatus 22, by opening the front cover 22*a* upward.

Each archive rack R1 and the sorting rack R2 are respectively housed in trays 171 and 172 that are movable in the front-rear direction. In the front face of the sample sorting apparatus 22, an opening S1 is provided so as to be located to the front of six pairs of the archive rack R1 and the tray 171, and the sorting rack R2 and the tray 171 (hereinafter referred to as "storage part"). Accordingly, the user can draw the trays 171 and 172 via the opening S1, and can take out/set the archive racks R1 and the sorting rack R2 from/on the trays 171 and 172.

Figure 5:
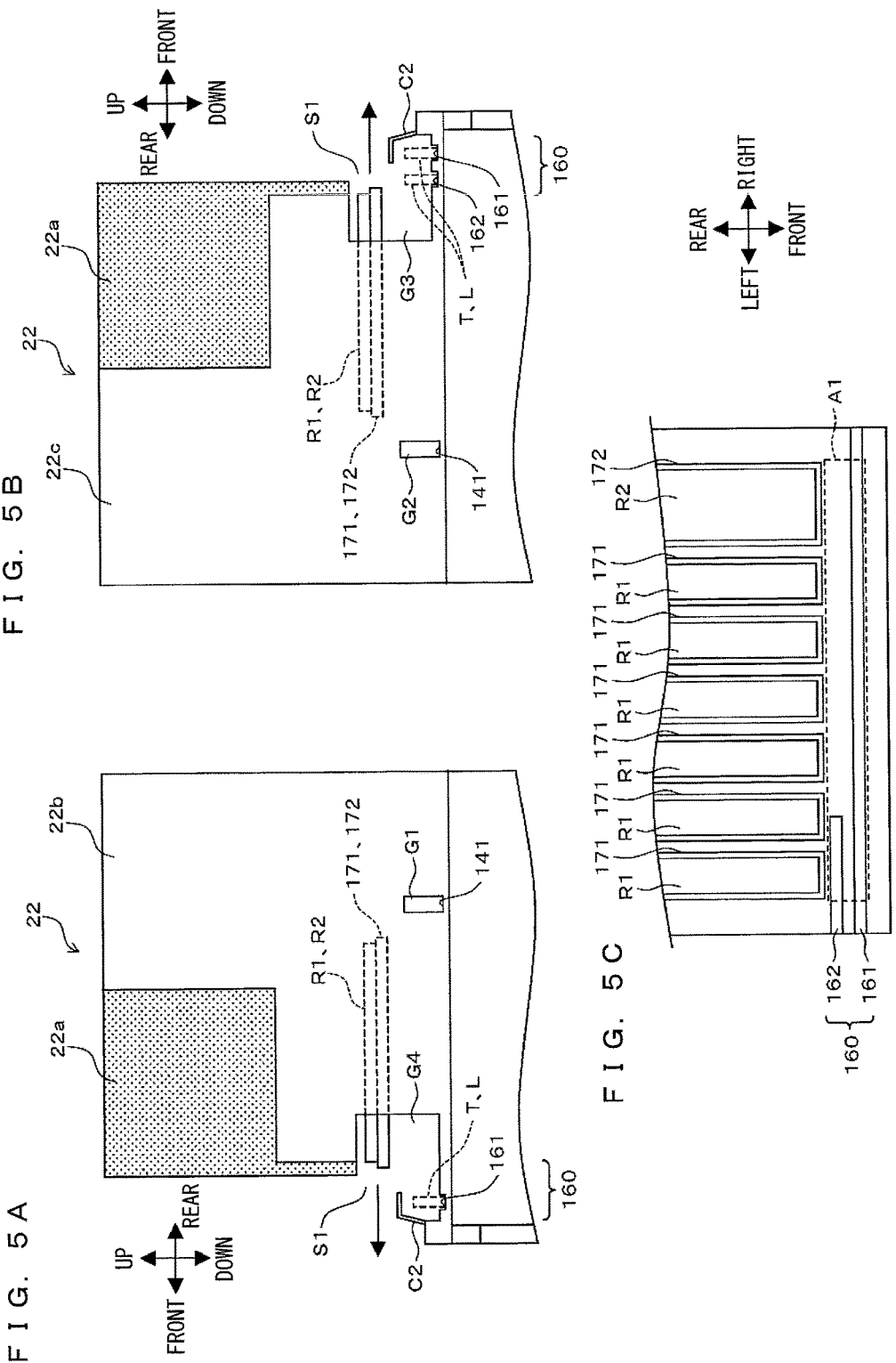
FIGS. 5A and 5B show side views of a structure of the sample sorting apparatus according to an embodiment.
FIG. 5C shows a plan view showing a positional relationship between a storage part and a transporter viewed from the vertical direction.

Each of FIGS. 5A and 5B shows a side view of the structure of the sample sorting apparatus 22.

With reference to FIG. 5A, at the right end of the sample sorting apparatus 22, there is provided a side face 22*b* that is parallel to a plane extending in the front-rear direction and the up-down direction. The side face 22*b* is provided with an inlet G1 for sending in a sample rack L sent out from the feeding unit 21, to the belt 141, and an exit G4 for sending out a sample rack L from the belt 161 to the feeding unit 21. With reference to FIG. 5B, at the left end of the sample sorting apparatus 22, there is provided a side face 22*c* that is parallel to a plane extending in the front-rear direction and the up-down direction. The side face 22*c* is provided with an outlet G2 for sending out a sample rack L from the belt 141 to the relay unit 23, and an entrance G3 for sending in a sample rack L sent out from the relay unit 23, to the belt 161 or 162. The entrance G3 and the exit G4 are continued to the opening S1.

Further, the storage part is located at a higher level than the transporter 160, the sample rack L transported on the transporter 160, and the sample container(s) T held in this sample rack L, and the cover C2. Therefore, the user can draw the trays 171 and 172 via the opening S1 and take out/set the archive racks R1 and the sorting rack R2, without blocking transportation of the sample container(s) T on the transporter 160.

FIG. 5C is a plan view showing a positional relationship between the storage part and the transporter 160 viewed from the vertical direction.

When a region of the transporter 160 corresponding to the width in the left-right direction of the storage part is defined as a region A1, the storage part does not overlap the region A1. Therefore, even when the belt 161 or 162 of the transporter 160 is stopped due to a failure or the like, the user can easily take out the sample container(s) T and the sample rack L stopped on the belt 161 or 162, by turning the cover C2 forward. That is, since the storage part does not overlap the region A1, the storage part does not exist on the route from which the sample container(s) T and the sample rack L on the belt 161 or 162 are taken out. Accordingly, the user can easily take out the sample container(s) T and the sample rack L.

Figure 6:
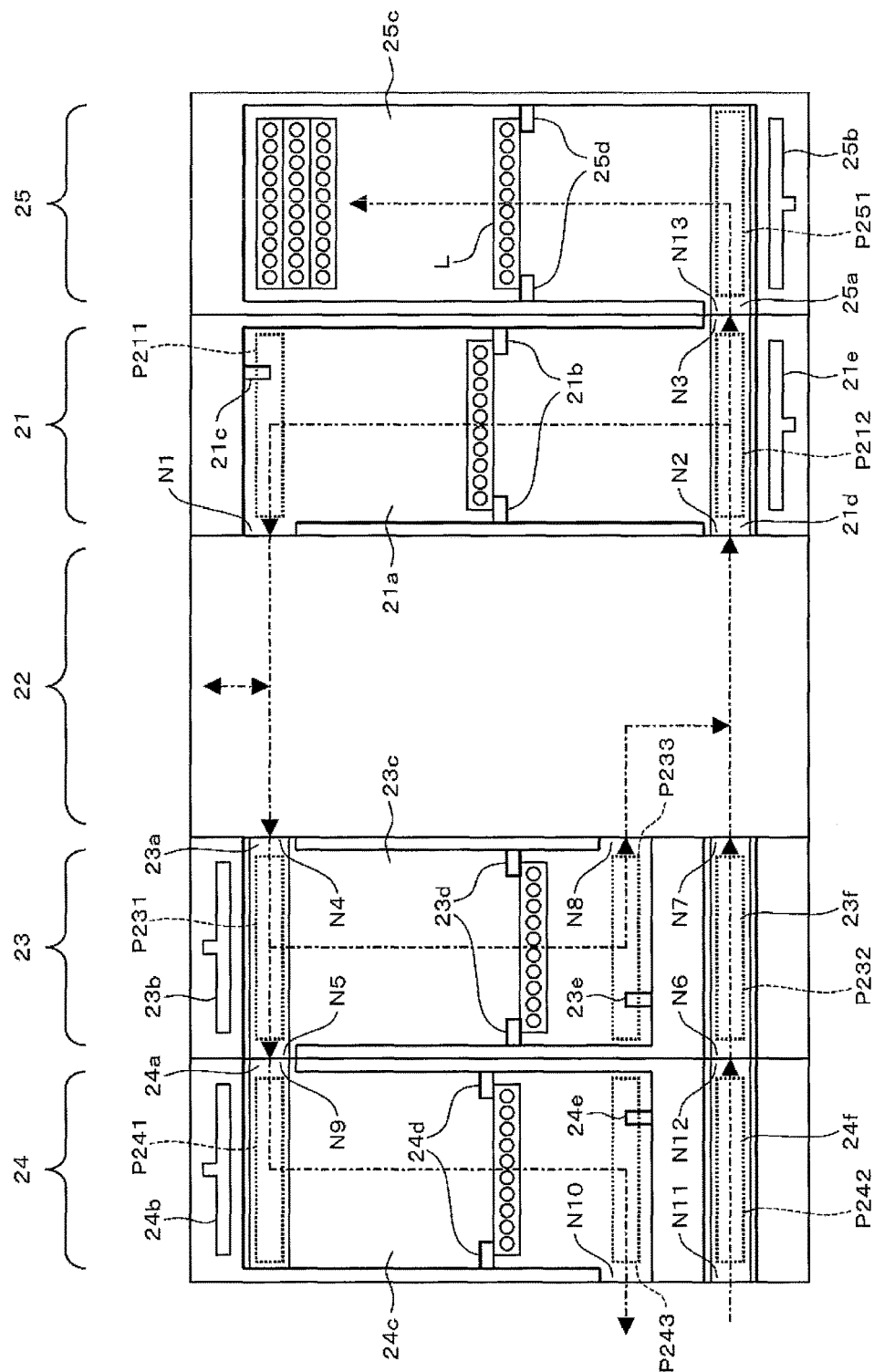
FIG. 6 shows structures of the feeding unit, the relay unit, the preprocessing unit and the collection unit according to an embodiment viewed from above.

FIG. 6 shows the structures of the feeding unit 21, the relay unit 23, the preprocessing unit 24, and the collection unit 25 viewed from above. It should be noted that, the inside of the sample sorting apparatus 22 is not shown for convenience.

In a rear portion and a front portion of the feeding unit 21, positions P211 and P212 are set, respectively. As also shown in FIG. 4, to the left of the position P211, a cutout N1 is formed, and to the left and right of the position P212, cutouts N2 and N3 are formed, respectively. The cutouts N1 and N2 are connected to the inlet G1 and the exit G4 of the sample sorting apparatus 22, respectively, and are configured to allow transportation of a sample rack L therethrough.

When a sample rack L is located in a transport path 21a of the feeding unit 21, this sample rack L is then located at the position P211 by a rack sending-in mechanism 21b. The sample rack L located at the position P211 is sent out to the sample sorting apparatus 22 via the cutout N1 by a rack sending-out mechanism 21c. On the other hand, a sample rack L sent out from the sample sorting apparatus 22 to the feeding unit 21 is located at the position P212 via the cutout N2 by a belt 21d. In a case where sample container(s) T are supported in the sample rack L located at the position P212, this sample rack L is pushed out to the transport path 21a by a rack pushing-out mechanism 21e. In a case where the sample rack L located at the position P212 is empty, this sample rack L is sent out to the collection unit 25 via the cutout N3 by the belt 21d.

In a rear portion and a front portion of the relay unit 23, and in a front portion of a transport path 23c, positions P231, P232, and P233 are set, respectively. To the right and left of the position P231, cutouts N4 and N5 are formed, respectively. To the left and right of the position P232, cutouts N6 and N7 are formed, respectively. To the right of the position P233, a cutout N8 is formed. The cutout N4 is continued to the outlet G2 of the sample sorting apparatus 22, and is configured to allow transportation of a sample rack L therethrough. The cutouts N7 and N8 are continued to the entrance G3 of the sample sorting apparatus 22, and are configured to allow transportation of a sample rack L therethrough.

A sample rack L sent out from the sample sorting apparatus 22 to the relay unit 23 is located at the position P231 via the cutout N4 by a belt 23a. In a case where sample container(s) T are held in the sample rack L located at the position P231, this sample rack L is transported to the preprocessing unit 24 via the cutout N5 by the belt 23a. In a case where the sample rack L located at the position P231 is empty, this sample rack L is pushed out to the transport path 23c by a rack pushing-out mechanism 23b, then located at the position P233 by a rack sending-in mechanism 23d, and then sent out to the sample sorting apparatus 22 via the cutout N8 by a rack sending-out mechanism 23e. On the other hand, a sample rack L sent out from the preprocessing unit 24 to the relay unit 23 is located at the position P232 via the cutout N6, to be sent out to the sample sorting apparatus 22 via the cutout N7 by a belt 23f.

Similarly to the relay unit 23, the preprocessing unit 24 is provided with cutouts N9 to N12. A sample rack L sent out from the relay unit 23 to the preprocessing unit 24 is located at a position P241 via the cutout N9 by a belt 24a, pushed out to a transport path 24c by a rack pushing-out mechanism 24b, then located at a position P243 by a rack sending-in mechanism 24d, and then sent out to the transporting unit 31 via the cutout N10 by a rack sending-out mechanism 24e. On the other hand, a sample rack L sent out from the transporting unit 31 to the preprocessing unit 24 is located at a position P242 via the cutout N11, to be sent out to the relay unit 23 via the cutout N12 by a belt 24f.

In a front portion of the collection unit 25, a position P251 is set. To the left of the position P251, a cutout N13 is formed. The cutout N13 is continued to the cutout N3 of the feeding unit 21, and is configured to allow transportation of a sample rack L therethrough. A sample rack L sent out from the feeding unit 21 to the collection unit 25 is located at the position P251 via the cutout N13 by a belt 25a, pushed out to a transport path 25c by a rack pushing-out mechanism 25b, transported rearward by a rack sending-in mechanism 25d, and then housed in the transport path 25c.

FIG. 7 shows an outline of the configuration of the feeding unit 21, the sample sorting apparatus 22, and the transport controller 7.

The sample sorting apparatus 22 includes a controller 221, a communication section 222, the bar code unit B, the container conveyor 130, a driving section 223, a sensor section 224, and a display input section 225. The controller 221 controls these components in the sample sorting apparatus 22 and receives signals outputted from these components in the sample sorting apparatus 22. Further, the controller 221 communicates with the transport controller 7 via the communication section 222.

The driving section 223 includes mechanisms for driving the belts 141, 161, and 162, the rack pushing-out mechanisms 151 and 152, and the rack sending-in mechanism 111 shown in FIG. 3, and in addition, a mechanism for transporting a sample rack L on the sample sorting apparatus 22, and a drive source for driving these mechanisms. The sensor section 224 includes sensors for detecting a sample rack L located at the positions P1 to P6.

The feeding unit 21 includes a controller 211, a communication section 212, a driving section 213, and a sensor section 214. The controller 211 controls these components in the feeding unit 21 and receives signals outputted from these components in the feeding unit 21. Further, the controller 211 communicates with the transport controller 7 via the communication section 212. It should be noted that the relay unit 23, the preprocessing unit 24, and the collection unit 25 have configurations similar to that of the feeding unit 21.

The transport controller 7 includes a controller 701, a communication section 702, a hard disk 703, and a display input section 704. The controller 701 communicates with the feeding unit 21, the sample sorting apparatus 22, the relay unit 23, the preprocessing unit 24, the collection unit 25, the transporting units 31 to 33, and the host computer 8, via the communication section 702.

Each of FIGS. 8A to 8D is a view for explaining transport routes of a sample rack L. In FIGS. 8A to 8D, transport of a sample rack L is shown by solid arrows, and transfer of a sample container T is shown by dashed arrows. Further, only the vicinity of the sample sorting apparatus 22 in the sample processing system 1 is shown in FIGS. 8A to 8D.

Figure 8A:
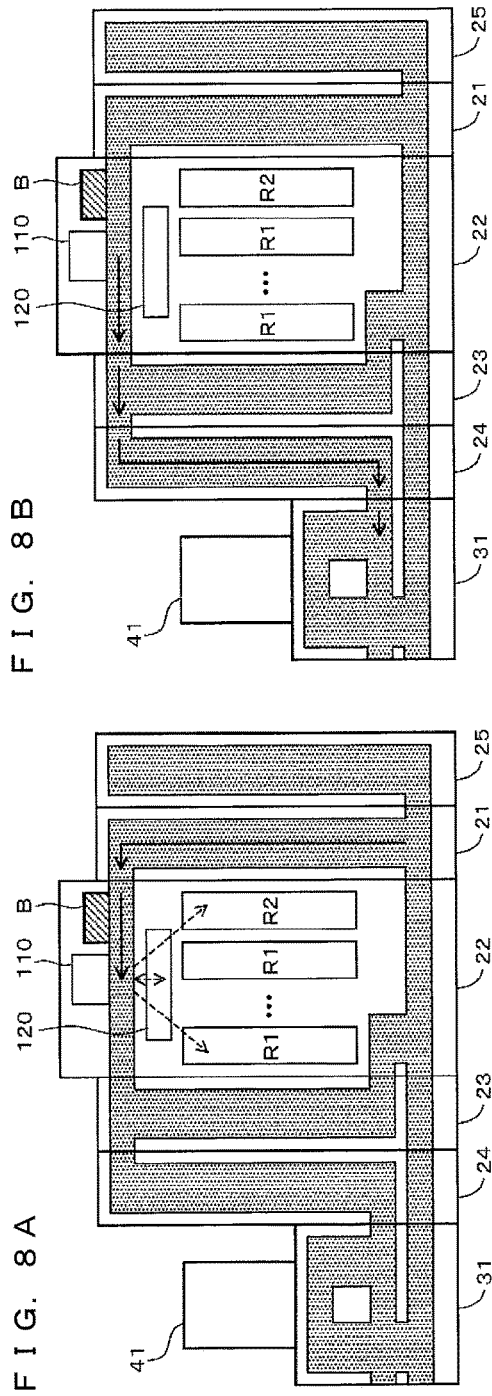
FIGS. 8A-8D show views for explaining transport routes of a sample rack according to an embodiment.

With reference to FIG. 8A, when a sample rack L holding sample container(s) T is placed in the feeding unit 21, this sample rack L is transported from the feeding unit 21 to the sample sorting apparatus 22. The sample sorting apparatus 22 transfers sample container(s) T held in this sample rack L. As a result, sample container(s) T are accordingly transferred to the buffer rack 120, the archive racks R1, or the sorting rack R2, or are not transferred and remain to be held in the sample rack L. Thereafter, the sample container(s) T transferred to the buffer rack 120 are transferred to an empty sample rack L as appropriate.

Figure 8B:
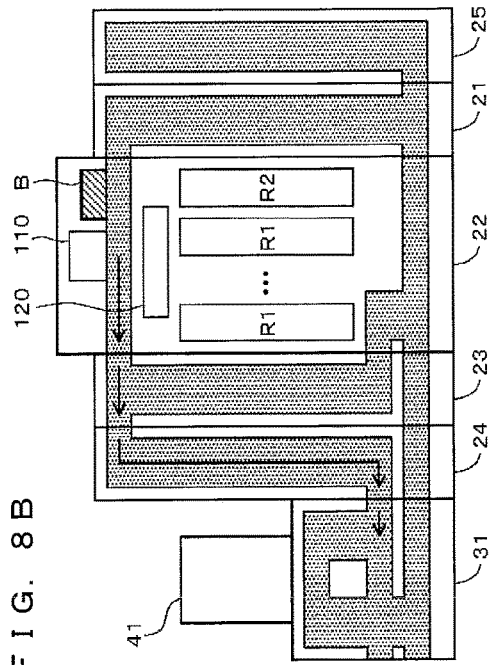

With reference to FIG. 8B, a sample rack L holding sample container(s) T is transported from the sample sorting apparatus 22, via the relay unit 23 and the preprocessing unit 24, to the transporting unit 31. Then, the sample container(s) T held in the sample rack L are subjected to processing by the measurement unit 41, 42 and/or the smear preparing apparatus 63.

Figure 8C:
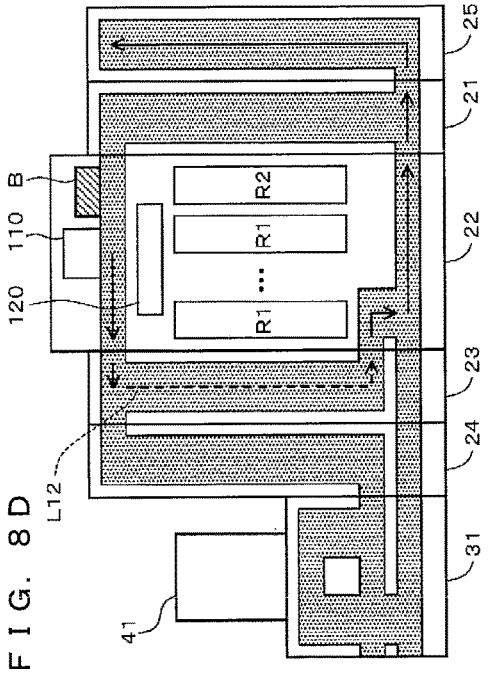

With reference to FIG. 8C, the sample rack L holding sample container(s) T that have been subjected to the processing by the measurement unit 41, 42 and/or the smear preparing apparatus 63 is transported from the transporting unit 31, via the preprocessing unit 24, the relay unit 23, and the sample sorting apparatus 22, to the feeding unit 21. As indicated by a line L11, the feeding unit 21 transports this sample rack L rearward and sends it out to the sample sorting apparatus 22. The sample sorting apparatus 22 transfers sample container(s) T held in this sample rack L. When a sample container T needs retesting, this sample container T is transferred to the buffer rack 120 or remains to be held in the sample rack L without being transferred. When a sample container T does not need retesting, and needs processing in an apparatus other than the sample processing system 1, this sample container T is transferred to the sorting rack R2. When a sample container T needs neither retesting nor processing in an apparatus other than the sample processing system 1, this sample container T is transferred to one of the archive racks R1.

Figure 8D:
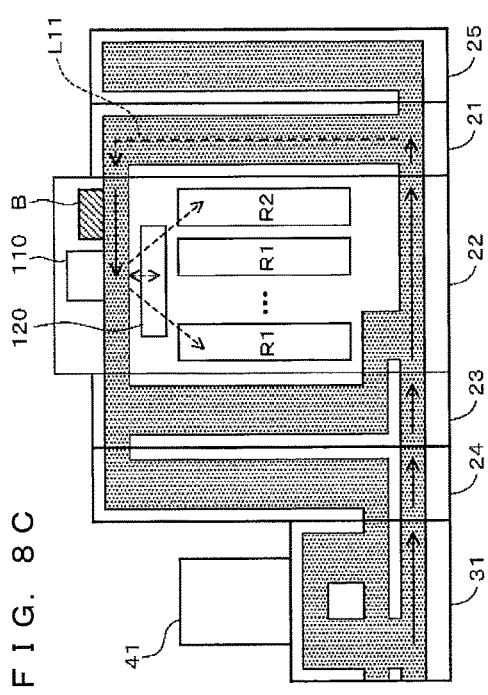

With reference to FIG. 8D, an empty sample rack L holding no sample container T is sent out from the sample sorting apparatus 22 to the relay unit 23. As indicated by a line L12, the relay unit 23 transports this sample rack L forward and send it out to the sample sorting apparatus 22. This sample rack L is transported rightward by the sample sorting apparatus 22 and the feeding unit 21, to be sent out to the collection unit 25. The collection unit 25 transports rearward the empty sample rack L sent out from the feeding unit 21, and houses it in the collection unit 25.

As described above, according to the present embodiment, sample container(s) T held in a sample rack L taken into the sample sorting apparatus 22 through the inlet G1 are transferred by the sample sorting apparatus 22 as appropriate, and then sent out to the relay unit 23 through the outlet G2. On the other hand, sample container(s) T whose sample(s) have been processed by the measurement unit 41, 42 and/or the smear preparing apparatus 63 are taken into the sample sorting apparatus 22 through the entrance G3 and then sent out, via the transporter 160 and through the exit G4, to the feeding unit 21. Then, the sample rack L sent out through the exit G4 is sent to the sample sorting apparatus 22 through the inlet G1 by the feeding unit 21 as appropriate, and then is subjected to transfer of the sample container(s) T again. Therefore, according to the present embodiment, transfer of sample container(s) T before sample processing and transfer of sample container(s) T after sample processing can be realized by the single sample sorting apparatus 22. Accordingly, increase of the installation area for the entire sample processing system 1 can be effectively suppressed. Further, a sample rack L returned from the measurement units 41 and 42 and the smear preparing apparatus 63 is conveyed, via the transporter 160 in the sample sorting apparatus 22, to the feeding unit 21. Thus, there is no need to separately provide a returning route for returning a sample container T from the measurement units 41 and 42 and the smear preparing apparatus 63 to the feeding unit 21. Therefore, compared with a case where a returning route is separately provided, increase of the installation area for the sample processing system 1 can be suppressed. In this manner, according to the present embodiment, transfer of sample container(s) T before sample processing and transfer of sample container(s) T after sample processing can be realized, while effectively suppressing increase of the installation area for the sample processing system 1.

Further, according to the present embodiment, when the transportation destination of sample container(s) T is the measurement unit 42 or the smear preparing apparatus 63, the container conveyor 130 transfers the sample container(s) T taken out from the sample rack L into the buffer rack 120. Then, the container conveyor 130 transfers sample container(s) T in the buffer rack 120, into an empty sample rack L. Thus, since desired sample container(s) T can be selected as appropriate from sample containers T held in the buffer rack 120 to be set in another sample rack L, transfer of sample container(s) T can be efficiently performed.

Further, according to the present embodiment, the inlet G1 and the exit G4 are provided on the same side face (the side face 22b) of the sample sorting apparatus 22. Therefore, simply by installing the feeding unit 21 so as to be adjacent to the side face 22b, a sample rack L can be transported between the sample sorting apparatus 22 and the feeding unit 21. Further, the outlet G2 and the entrance G3 are provided on the same side face (the side face 22c) of the sample sorting apparatus 22. Therefore, simply by installing the relay unit 23 so as to be adjacent to the side face 22c, a sample rack L can be transported between the sample sorting apparatus 22 and the relay unit 23.

Further, according to the present embodiment, the side face 22c is arranged opposite to the side face 22b, relative to the sample sorting apparatus 22. Accordingly, the sample sorting apparatus 22, the feeding unit 21, and the relay unit 23 can be linearly arranged.

Further, according to the present embodiment, the opening S1 is provided to the front of six pairs of the archive rack R1 and the tray 171, and the sorting rack R2 and the tray 171 (the storage part). Moreover, the storage part is located at a higher level than the transporter 160, the sample rack L transported on the transporter 160, and the sample container(s) T held in this sample rack L, and the cover C2. Accordingly, even when a sample rack L is being transported from the entrance G3 toward the exit G4, the user can draw the storage part forward and take out sample container(s) T outside, without the storage part blocking transportation of the sample container(s) T on the transporter 160.

Further, according to the present embodiment, as shown in FIG. 6, the feeding unit 21 sends a sample rack L placed on the transport path 21a to the position P211 by means of the rack sending-in mechanism 21b, and then sends the sample rack L via the cutout N1 to the inlet G1 of the sample sorting apparatus 22 by means of the rack sending-out mechanism 21c. On the other hand, the feeding unit 21 transports a sample rack L sent out through the exit G4 of the sample sorting apparatus 22 to the position P212 via the cutout N2 by means of the belt 21d, and then pushes out the sample rack L to the transport path 21a by means of the rack pushing-out mechanism 21e. Accordingly, a sample rack L sent out through the exit G4 can be sent into the sample sorting apparatus 22 through the inlet G1 again. Thus, sample container(s) T having been subjected to sample processing can be transferred again.

Further, according to the present embodiment, the relay unit 23 transports a sample rack L sent out through the outlet G2, to the entrance G3 as indicated by the line L12 (see FIG. 8D) not via the measurement units 41 and 42 and the smear preparing apparatus 63. Accordingly, for example, it is possible to prevent a sample rack L, such as an empty sample rack L, that need not be transported, from being transported to these units and apparatus.

Further, according to the present embodiment, as shown in FIG. 6, a sample rack L sent out through the exit G4 of the sample sorting apparatus 22 is transported rightward by the belt 21d, to be sent to the collection unit 25 via the cutouts N3 and N13. Accordingly, a sample rack L that need not be transported to the measurement unit 41, 42 and/or the smear preparing apparatus 63 again can be sent to the collection unit 25. Further, the user can efficiently collect empty sample racks L, by accessing the collection unit 25.

<Modification 1> In the above embodiment, as shown in FIGS. 5A to 5C, when viewed from the vertical direction, the storage part is configured not to overlap the region A1. However, the storage part may be configured to overlap the region A1.

Figure 9:
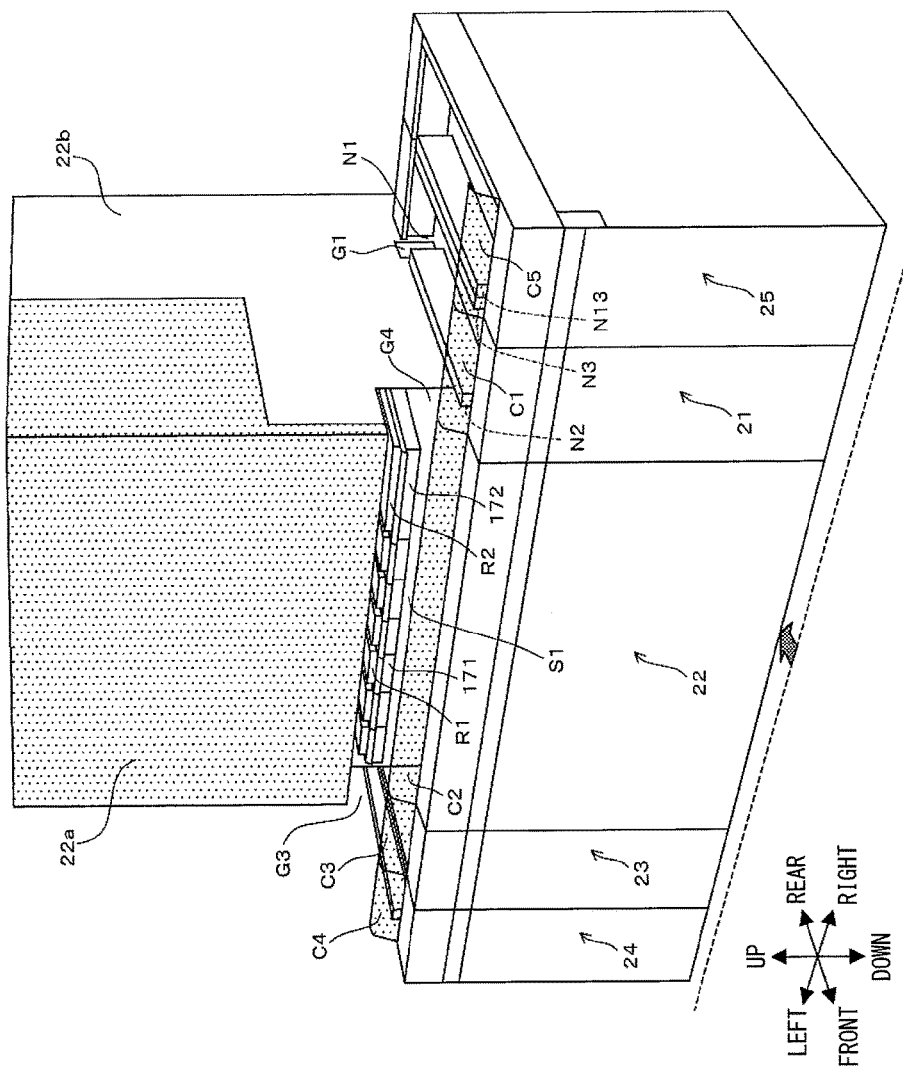
FIG. 9 is a perspective view showing external structures of the feeding unit, the sample sorting apparatus, the relay unit, the preprocessing unit, and the collection unit according to modification 1.
Figure 10B:
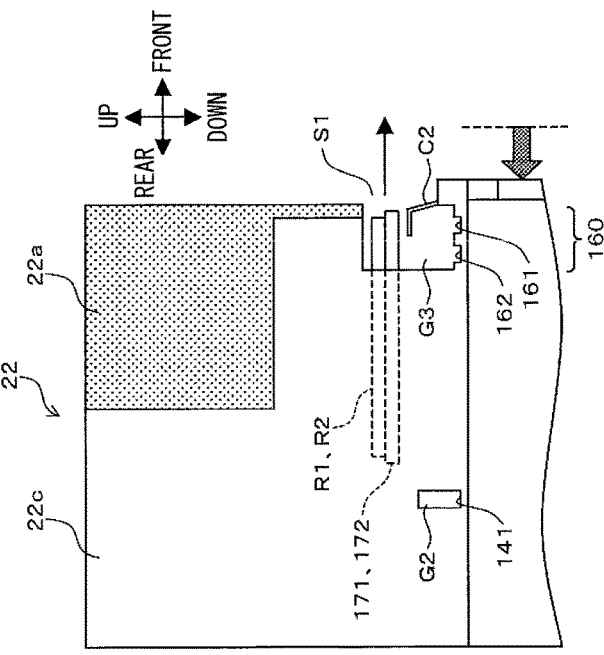
FIGS. 10A and 10B show side views of a structure of the sample sorting apparatus according to modification 1.
Figure 10A:
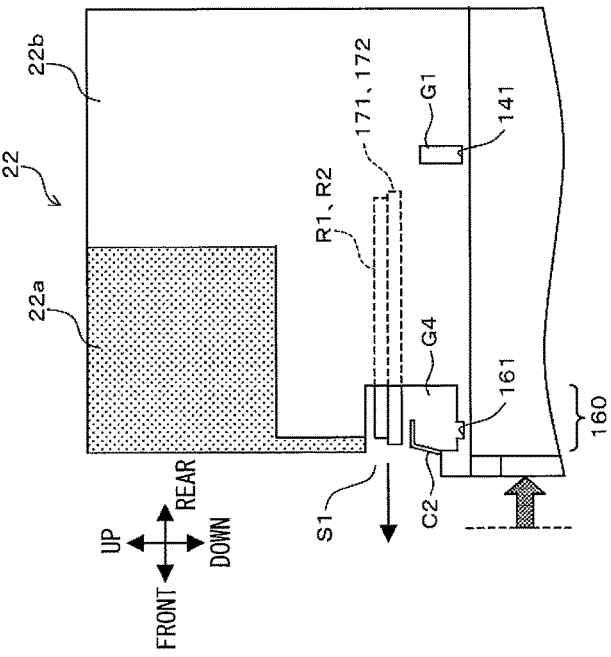
Figure 10C:
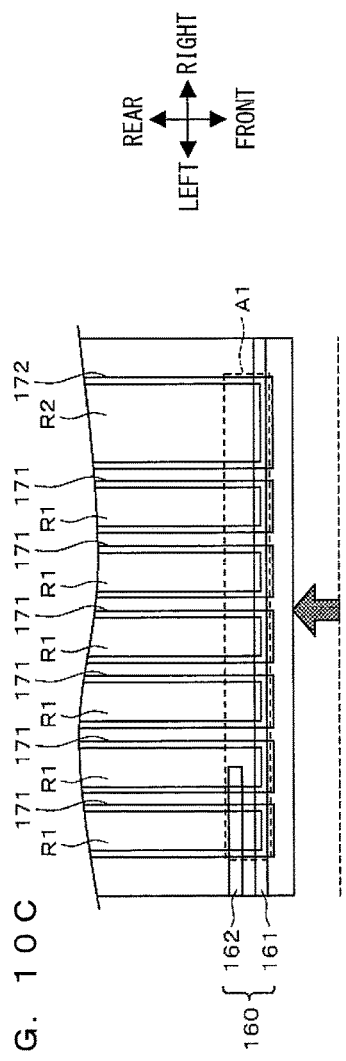
FIG. 10C shows a plan view showing a positional relationship between the storage part and the transporter viewed from the vertical direction.

In the present modification, as shown in FIG. 9 and FIGS. 10A and 10B, the front face of the sample sorting apparatus 22, the belts 161 and 162, and the cover C2 are located rearward compared to those in the above embodiment. The storage part when viewed from the vertical direction overlaps the entirety of the region A1 as shown in FIG. 10C.

According to the present modification, as in the above embodiment, the user can take out and set the archive racks R1 and the sorting rack R2, without blocking transportation of sample container(s) T on the transporter 160. Further, according to the present modification, since the storage part overlaps the region A1, the size of the sample sorting apparatus 22 in the front-rear direction can be reduced compared with that in the above embodiment, and thus, the installation area for the sample sorting apparatus 22 can be reduced.

In the present modification, the storage part overlaps the entirety of the region A1 when viewed from the vertical direction. Instead, at least a part of the storage part may overlap a part of the region A1. Also in this case, compared with the above embodiment, the size of the sample sorting apparatus 22 in the front-rear direction can be reduced, and thus, the installation area for the sample sorting apparatus 22 can be reduced.

<Modification 2> In modification 1 above, as shown in FIG. 9 and FIGS. 10A and 10B, the opening S1 to the front of the storage part is configured to be continued to the entrance G3 and the exit G4. However, the opening to the front of the storage part may not be continued to the entrance G3 and the exit G4.

Figure 11:
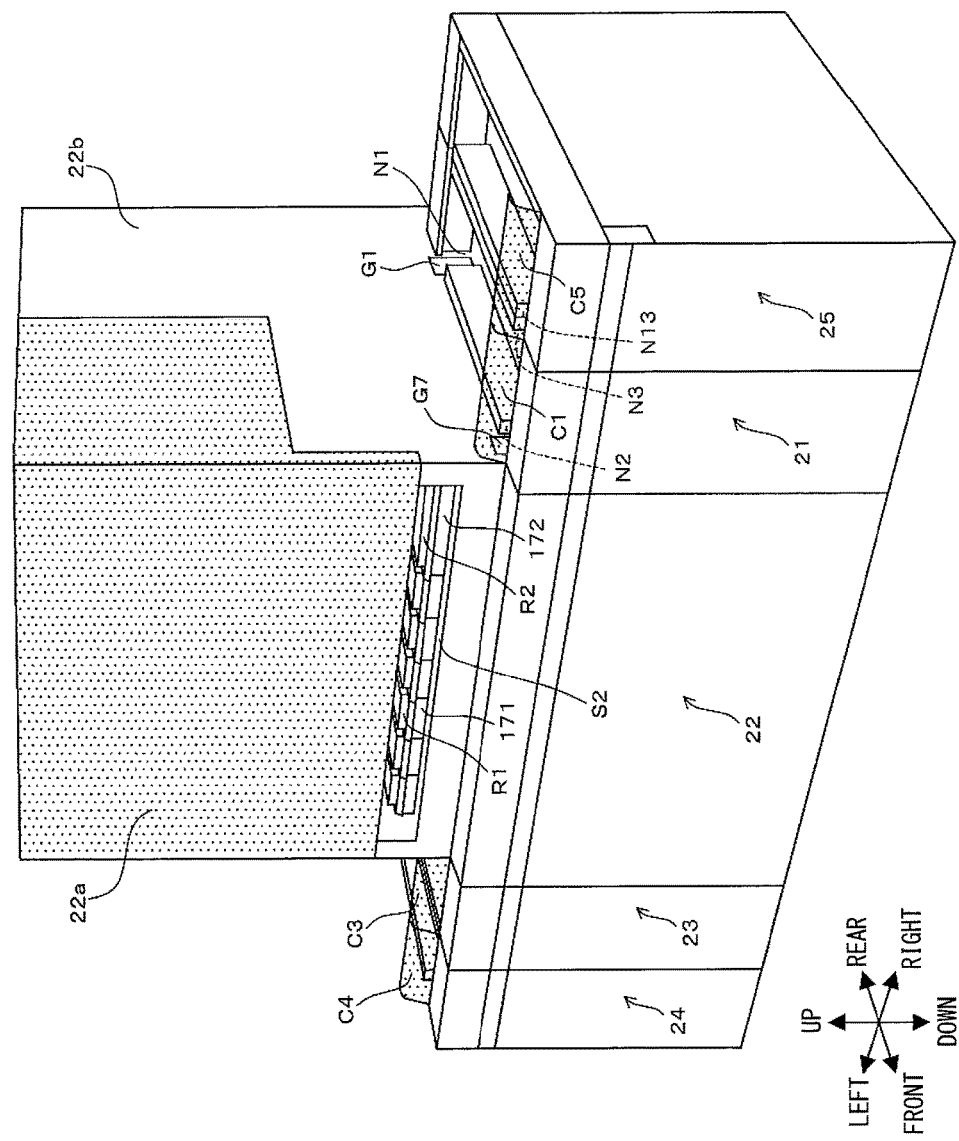
FIG. 11 is a perspective view showing external structures of the feeding unit, the sample sorting apparatus, the relay unit, the preprocessing unit, and the collection unit according to modification 2.
Figure 12B:
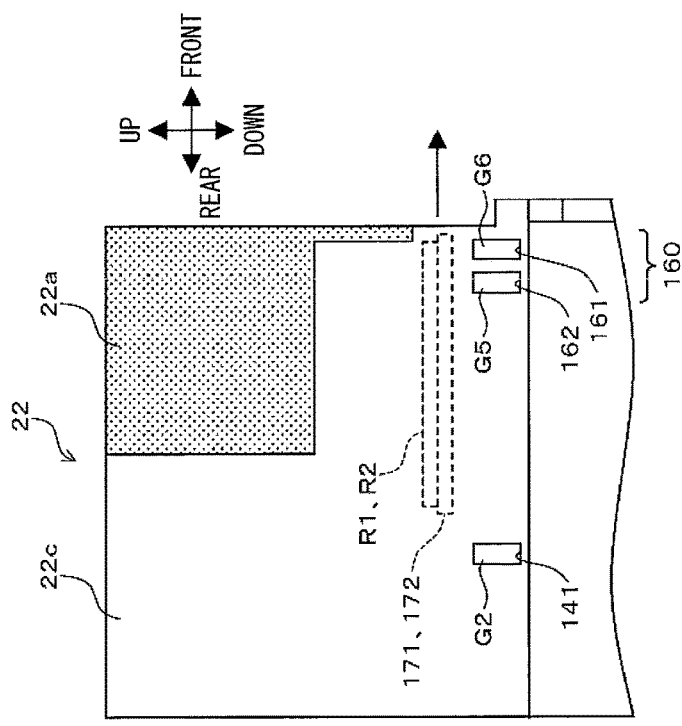
FIGS. 12A and 12B show side views of a structure of the sample sorting apparatus according to modification 2.
Figure 12A:
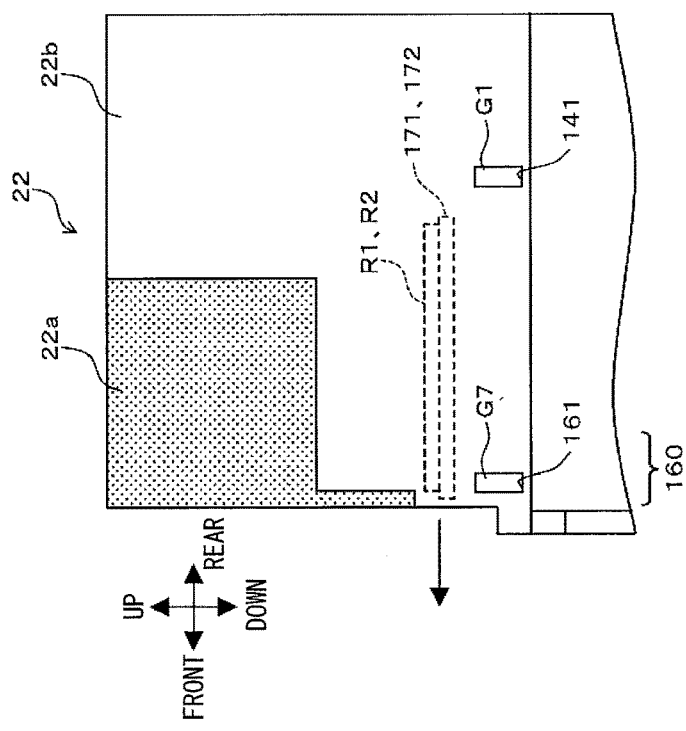

In the present modification, as shown in FIG. 11, an opening S2 is provided in the front face of the sample sorting apparatus 22, so as to be located to the front of the storage part. As shown in FIG. 12A, the side face 22b is provided with, instead of the exit G4, an outlet G7 for sending out a sample rack L from the belt 161 to the feeding unit 21. As shown in FIG. 12B, the side face 22c is provided with, instead of the entrance G3, inlets G5 and G6 for respectively sending a sample rack L sent out from the relay unit 23 to the belts 162 and 161. The opening S2 is continued to none of the inlets G5 and G6 and the outlet G7.

According to the present modification, since the user cannot touch the transporter 160 from the front side, the user can be prevented from touching by mistake a sample rack L and sample container(s) T on the belt 161 or 162.

Embodiments of the present invention have been described. However, the embodiment of the present invention is not limited thereto.

For example, the above embodiment has shown an example in which blood is measured in the measurement units 41 and 42. However, urine may be measured by the measurement units 41 and 42. That is, the present invention can be applied to a sample processing system that includes measurement units for measuring urine. Further, the present invention can be applied to a clinical sample processing system that includes measurement units for measuring other clinical samples.

Figure 13A:
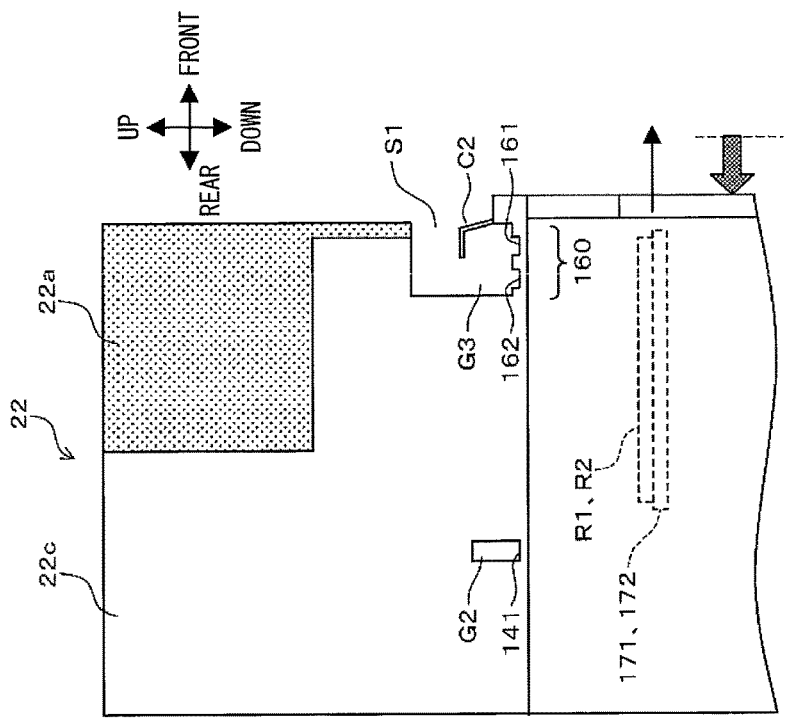
FIGS. 13A and 13B show side views of a structure of the sample sorting apparatus according to another modification.
Figure 13B:
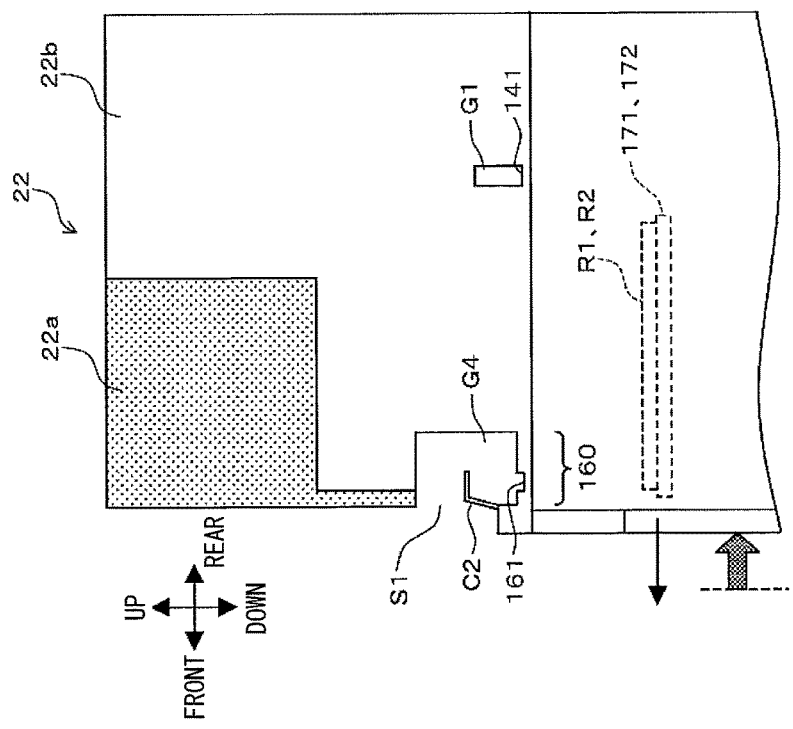

In the above embodiment, the storage part composed of the archive racks R1 and the sorting rack R2 and the trays 171 and 172 is located above the belts 161 and 162. However, the present invention is not limited thereto. The storage part may be located below the belts 161 and 162. In this case, as shown in FIGS. 13A and 13B, if the storage part viewed from the vertical direction is configured to overlap the region A1 (see FIG. 10C) of the transporter 160 as in modification 1, the size of the sample sorting apparatus 22 in the front-rear direction can be reduced, and thus, the installation area for the sample sorting apparatus 22 can be reduced. It should be noted that in the configuration shown in FIGS. 13A and 13B, for smoothly taking out/setting a sample container T from/to the storage part by the container conveyor 130, space needs to be provided between the transporter 160 and the storage part. Further, when viewed from the vertical direction, the storage part may overlap a part of the region A1 of the transporter 160.

Figure 14:
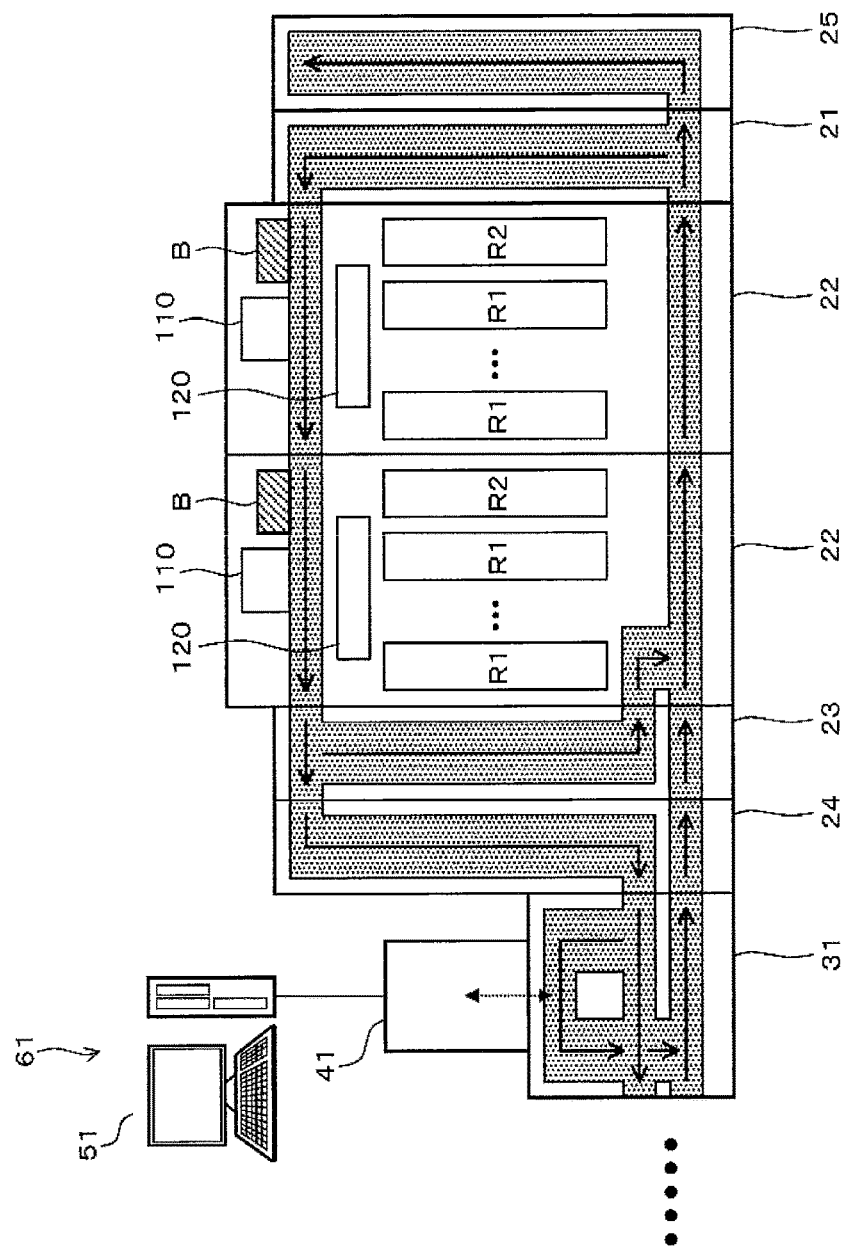
FIG. 14 shows a structure of the sample processing system according to another modification viewed from above.

In the above embodiment, as shown in FIG. 1, the single sample sorting apparatus 22 is included in the sample processing system 1. However, the present invention is not limited thereto. As shown in FIG. 14, a plurality of the sample sorting apparatuses arranged side by side may be included in the sample processing system 1. In this case, the plurality of the sample sorting apparatuses 22 are arranged so as to be adjacent to each other such that the outlet G2 and the entrance G3 of each upstream sample sorting apparatus 22 are respectively continued to the inlet G1 and the exit G4 of its downstream sample sorting apparatus 22. In this case, in the sample sorting apparatus(s) 22 (the right sample sorting apparatus 22 in the case of FIG. 14) other than the most downstream sample sorting apparatus 22, the belt 162 may be omitted. Also in this case, the effects similar to those in the above embodiment can be obtained.

In the above embodiment, each sample container T taken out from a sample rack L that was sent into the transporter 140 is conveyed to the buffer rack 120, and sample container(s) T taken out from the buffer rack 120 are transferred to an empty sample rack L in accordance with their transportation destination. However, the present invention is not limited thereto. Each sample container T taken out from a sample rack L that was sent into the transporter 140 is conveyed to the buffer rack 120, and the sample container may be transferred to a setting position in the original sample rack L different from a setting position from which the sample container T was taken out. Further, each sample container T taken out from a sample rack L that was sent into the transporter 140 may be transferred to an empty sample rack L, not via the buffer rack 120. Further, each sample container T taken out from a sample rack L that was sent into the transporter 140 may be transferred simply to another setting position within the sample rack L, without transferring the sample container T into the buffer rack 120 or an empty sample rack L. Further, in the above embodiment, only empty sample racks L are collected in the collection unit 25. However, the present invention is not limited thereto. For example, sample racks L only holding sample container(s) T each containing a sample that has a predetermined result may be collected in the collection unit 25.

In the above embodiment, the sample sorting apparatus 22 and the feeding unit 21 are separately provided. However, the feeding unit 21 may be integrated with the sample sorting apparatus 22. Still further, the collection unit 25 and the relay unit 23 may be integrated with the sample sorting apparatus 22.

In the above embodiment, the two measurement units 41 and 42, and the one smear preparing apparatus 63 are arranged on the downstream side of the sample sorting apparatus 22. However, the type, the number, and the arrangement positions of sample processing apparatuses connected to the sample sorting apparatus 22 are not limited thereto. For example, the number of measurement units arranged may be one, or three or more. Presence/absence or the number of smear preparing apparatuses may also be changed. Still further, blood sedimentation measurement apparatuses may be added, and the sample processing apparatuses may be arranged on the upstream side.

In addition to the above, various modifications of the embodiment of the present invention may be made as appropriate, without departing from the scope of the technical idea defined by the claims.

What is claimed is:

1. A sample sorting apparatus used in a sample processing system comprising a sample supplying apparatus, a sample processing apparatus, and a transporting apparatus connected to the sample processing apparatus, the sample sorting apparatus comprising:
   a first entrance for receiving a sample rack from the sample supplying apparatus;
   a first exit for sending the sample rack received through the first entrance to the transporting apparatus;
   a first transporter configured to transport the sample rack from the first entrance to the first exit;
   a container conveyor configured to take out at least one sample container from the sample rack on the first transporter when transporting the sample rack from the first entrance to the first exit, and the container conveyor is configured to set at least a same one taken out or a different sample container back on the sample rack;
   a buffer rack having a plurality of holders to hold a plurality of sample containers, wherein the buffer rack is for holding the at least one sample container taken out from the sample rack before the at least one sample container is transferred to a different setting position in the sample rack from which the at least one sample container was taken out;
   a second entrance for receiving an incoming sample rack from the transporting apparatus;
   a second exit for sending the incoming sample rack received through the second entrance to the sample supplying apparatus; and
   a second transporter configured to transport the incoming sample rack from the second entrance to the second exit.

2. The sample sorting apparatus of claim 1, wherein the first entrance and the second exit are provided in a first side face of a body of the sample sorting apparatus, and the first exit and the second entrance are provided in a second side face of the body of the sample sorting apparatus.

3. The sample sorting apparatus of claim 2, wherein the second side face is arranged opposite to the first side face, relative to the body of the sample sorting apparatus.

4. The sample sorting apparatus of claim 1, comprising a container storage part for storing a portion from one or more sample containers which are not to be supplied to the sample processing apparatus.

5. The sample sorting apparatus of claim 4, wherein the container conveyor conveys, the portion from among one or more sample containers held in the sample rack which are not to be supplied to the sample processing apparatus, to the container storage part.

6. The sample sorting apparatus of claim 5, wherein the container storage part is configured to be able to be drawn from outside, and is arranged so as not to block transportation of sample container(s) on the transporter when the container storage part is drawn from the outside.

7. The sample sorting apparatus of claim 4, wherein the container storage part is arranged to overlap without touching from above or below, a transport path of the transporter.

8. A sample processing system comprising:
   a sample sorting apparatus;
   a sample supplying apparatus which supplies a sample rack to the sample sorting apparatus;
   a sample processing apparatus which processes a sample in a sample container held in the sample rack; and
   a transporting apparatus arranged between the sample sorting apparatus and the sample processing apparatus,
   wherein the sample sorting apparatus comprises:
   a first entrance for receiving a sample rack from the sample supplying apparatus;
   a first exit for sending the sample rack received through the first entrance to the transporting apparatus;
   a first transporter configured to transport the sample rack from the first entrance to the first exit;
   a container conveyor configured to take out at least one sample container from the sample rack on the first transporter when transporting the sample rack from the first entrance to the first exit, and the container conveyor is configured to set at least a same one taken out or a different sample container back on the sample rack;
   a buffer rack having a plurality of holders to hold a plurality of sample containers, wherein the buffer rack is for holding the at least one sample container taken out from the sample rack before the at least one sample container is transferred to a different setting position in the sample rack from which the at least one sample container was taken out;
   a second entrance for receiving an incoming sample rack from the transporting apparatus;
   a second exit for sending the incoming sample rack received through the second entrance to the sample supplying apparatus; and
   a second transporter configured to transport the incoming sample rack from the second entrance to the second exit.

9. The sample processing system of claim 8, wherein the sample supplying apparatus comprises:
   a supply part continued to the first entrance of the sample sorting apparatus;
   a transport path for transporting the sample rack that has been fed thereto, to the supply part;
   a sending-out part which sends out the sample rack transported to the supply part, into the sample sorting apparatus through the first entrance; and
   a receiving part which is connected to the second exit of the sample sorting apparatus and guides the incoming sample rack sent through the second exit, to the transport path of the sample supplying apparatus.

10. The sample processing system of claim 8, wherein the transporting apparatus comprises a transport route for transporting the sample rack sent out through the first exit, to the second entrance without passing through the sample processing apparatus.

11. The sample processing system of claim 10, further comprising
   a rack housing apparatus arranged adjacent to the sample supplying apparatus for housing one or more sample racks, wherein
   the sample supplying apparatus and the rack housing apparatus respectively comprise communication parts which are in communication with each other and which allow transportation of the one or more sample rack therethrough, and the sample supplying apparatus further comprises a conveyor which conveys the incoming sample rack sent out through the second exit of the sample sorting apparatus, to the rack housing apparatus via the communication parts.

12. The sample processing system of claim 8, comprising a plurality of the sample sorting apparatuses, wherein the plurality of the sample sorting apparatuses are arranged adjacent to each other, such that the first exit and the second entrance of each upstream sample sorting apparatus are respectively connected to the first entrance and the second exit of a downstream sample sorting apparatus thereof, the sample supplying apparatus is arranged adjacent to a most upstream sample sorting apparatus, sends out the sample rack into the most upstream sample sorting apparatus through the first entrance thereof, and receives the incoming sample rack sent out through the second exit of the most upstream sample sorting apparatus, and the transporting apparatus is arranged adjacent to a most downstream sample sorting apparatus, transports the sample rack sent out through the first exit of the most downstream sample sorting apparatus, to the sample processing apparatus, and transports the incoming sample rack for which processing in the sample processing apparatus has been completed, to the second entrance of the most downstream sample sorting apparatus.

* * * * *